United States Patent
O'Driscoll et al.

(10) Patent No.: US 11,309,744 B2
(45) Date of Patent: Apr. 19, 2022

(54) SYSTEMS AND METHODS FOR PROVIDING WIRELESS POWER TO DEEP IMPLANTED DEVICES

(71) Applicant: Verily Life Sciences LLC, South San Francisco, CA (US)

(72) Inventors: Stephen O'Driscoll, San Francisco, CA (US); Jiang Zhu, Cupertino, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 157 days.

(21) Appl. No.: 15/696,838

(22) Filed: Sep. 6, 2017

(65) Prior Publication Data
US 2018/0076670 A1    Mar. 15, 2018

Related U.S. Application Data

(60) Provisional application No. 62/393,081, filed on Sep. 11, 2016.

(51) Int. Cl.
*H02J 50/20* (2016.01)
*H02J 7/02* (2016.01)
(Continued)

(52) U.S. Cl.
CPC ............ *H02J 50/20* (2016.02); *A61N 1/3787* (2013.01); *H02J 7/025* (2013.01); *H02J 50/12* (2016.02);
(Continued)

(58) Field of Classification Search
CPC .......... H01Q 1/273; H01Q 7/00; H01Q 19/00; H01Q 3/2635; H01Q 3/446; H02J 50/10;
(Continued)

(56) References Cited

U.S. PATENT DOCUMENTS 6,099,482 A    8/2000 Brune et al.
8,373,252 B1*  2/2013 DeBaets ............ H01L 23/5223
                                                        257/532
(Continued)

FOREIGN PATENT DOCUMENTS

CN    1721014      1/2006
CN    101005800    7/2007
(Continued)

OTHER PUBLICATIONS

International Application No. PCT/US2017/050551, "International Search Report and Written Opinion", dated Nov. 24, 2017, 16 pages.
(Continued)

*Primary Examiner* — Rexford N Barnie
*Assistant Examiner* — Brian K Baxter
(74) *Attorney, Agent, or Firm* — Kilpatrick Townsend & Stockton LLP

(57) ABSTRACT

The present disclosure relates to systems and methods for providing wireless power to implanted devices. Consistent with some embodiments, a power system for providing wireless power to a device implanted in a body of an individual includes a first antenna loop that produces a first electromagnetic wave and at least one second antenna loop that produces a second electromagnetic wave. The first and second electromagnetic waves may interfere with one another to produce an interference pattern including interference maxima. Further, a location of at least one of the interference maxima may be at or substantially close to the device implanted in the body of the individual. A broad distribution pattern at the surface of the skin can reduce the specific absorption rate of the transmission, while focusing the transmission toward the implanted device improves the antenna system's transfer efficiency.

18 Claims, 10 Drawing Sheets
(6 of 10 Drawing Sheet(s) Filed in Color)

(51) Int. Cl.
| | |
|---|---|
| *H02J 50/23* | (2016.01) |
| *H02J 50/12* | (2016.01) |
| *A61N 1/378* | (2006.01) |
| A61B 5/00 | (2006.01) |
| *H02J 50/40* | (2016.01) |
| A61N 1/372 | (2006.01) |

(52) U.S. Cl.
CPC ............ *H02J 50/23* (2016.02); *A61B 5/0031* (2013.01); *A61B 2560/0219* (2013.01); *A61N 1/37229* (2013.01); *H02J 50/40* (2016.02)

(58) Field of Classification Search
CPC .. H02J 5/005; H02J 17/00; H02J 50/20; H02J 50/23; H02J 7/025; H02J 50/40; H04B 5/0037; H04B 5/0075; A61B 5/4064; A61B 2560/0219; A61B 5/0031; H01F 38/14; B60L 11/182; A61N 1/3787; A61N 1/37229
USPC ........................................................ 307/104
See application file for complete search history.

(56) References Cited

U.S. PATENT DOCUMENTS

| | | | |
|---|---|---|---|
| 8,634,928 B1* | 1/2014 | O'Driscoll | A61N 1/37229 607/33 |
| 9,672,393 B1 | 6/2017 | Zhu et al. | |
| 9,812,890 B1* | 11/2017 | Leabman | H02J 50/80 |
| 9,884,180 B1 | 2/2018 | Ho et al. | |
| 10,075,008 B1* | 9/2018 | Bell | H02J 50/90 |
| 10,099,049 B2 | 10/2018 | Ho et al. | |
| 10,230,266 B1 | 3/2019 | Leabman et al. | |
| 10,263,432 B1 | 4/2019 | Leabman et al. | |
| 10,291,055 B1 | 5/2019 | Bell et al. | |
| 10,291,066 B1 | 5/2019 | Leabman et al. | |
| 2005/0228268 A1 | 10/2005 | Cole | |
| 2007/0149162 A1* | 6/2007 | Greene | H03F 3/24 455/343.1 |
| 2008/0103558 A1 | 5/2008 | Wenzel et al. | |
| 2009/0134712 A1* | 5/2009 | Cook | H02J 50/12 307/104 |
| 2010/0033021 A1 | 2/2010 | Bennett et al. | |
| 2010/0114253 A1* | 5/2010 | Wahlstrand | A61M 5/14276 607/61 |
| 2011/0281535 A1* | 11/2011 | Low | H02J 7/025 455/129 |
| 2012/0228563 A1* | 9/2012 | Fuller | F41H 13/0043 252/582 |
| 2013/0194540 A1* | 8/2013 | Pugh | H01Q 1/22 351/159.03 |
| 2013/0200721 A1* | 8/2013 | Kurs | H02J 50/12 307/104 |
| 2013/0307753 A1* | 11/2013 | Andrenko | H01Q 1/243 343/904 |
| 2014/0028111 A1 | 1/2014 | Hansen et al. | |
| 2014/0125275 A1 | 5/2014 | Low et al. | |
| 2014/0292587 A1* | 10/2014 | Yarga | H01Q 1/243 343/702 |
| 2014/0313099 A1* | 10/2014 | Pajona | H01Q 5/50 343/852 |
| 2015/0295314 A1* | 10/2015 | Oh | H01Q 1/243 343/866 |
| 2015/0333413 A1 | 11/2015 | Piazza et al. | |
| 2015/0333529 A1 | 11/2015 | Leabman | |
| 2016/0087458 A1* | 3/2016 | Grbic | H02J 5/005 307/104 |
| 2016/0104941 A1* | 4/2016 | Lee | H01Q 1/1228 343/702 |
| 2016/0126744 A1* | 5/2016 | Jeong | H02J 17/00 307/104 |
| 2016/0220828 A1* | 8/2016 | Yan Poon | A61N 1/3787 |
| 2016/0344238 A1* | 11/2016 | Yeh | A61N 1/3787 |
| 2016/0352000 A1* | 12/2016 | Ohno | H01Q 1/38 |
| 2017/0038463 A1* | 2/2017 | Grbic | G01S 17/026 |
| 2017/0100056 A1* | 4/2017 | Zhu | G06K 7/10356 |
| 2017/0230084 A1 | 8/2017 | Zhu et al. | |
| 2017/0272123 A1 | 9/2017 | Zhu et al. | |
| 2017/0288475 A1* | 10/2017 | Lee | H02J 50/90 |
| 2017/0331330 A1* | 11/2017 | Yeo | H01Q 9/0407 |
| 2019/0150884 A1* | 5/2019 | Maharbiz | A61B 5/0031 |
| 2020/0101296 A1* | 4/2020 | Forsell | A61F 7/12 |

FOREIGN PATENT DOCUMENTS

| | | |
|---|---|---|
| CN | 102112045 | 6/2011 |
| CN | 104736053 | 6/2015 |
| CN | 104767284 | 7/2015 |
| CN | 104941017 | 9/2015 |
| JP | 2011514221 | 5/2011 |
| JP | 2015112169 | 6/2015 |
| WO | 2009009559 | 1/2009 |
| WO | 2009115102 | 9/2009 |
| WO | 2010042054 | 4/2010 |
| WO | 2011046674 | 4/2011 |
| WO | 2015039108 | 3/2015 |
| WO | 2015179225 | 11/2015 |
| WO | 2017160560 | 9/2017 |

OTHER PUBLICATIONS

U.S. Appl. No. 15/071,113 , "Advisory Action", dated Jan. 28, 2019, 2 pages.
PCT/US2017/021403 , "International Preliminary Report on Patentability", dated Sep. 27, 2018, 8 pages.
PCT/US2017/021403 , "International Search Report and Written Opinion", dated May 23, 2017, 14 pages.
International Application No. PCT/US2017/050551, "International Preliminary Report on Patentability", dated Mar. 21, 2019, 11 pages.
European Application No. 17771637.0 , "Office Action", dated Apr. 17, 2020, 6 pages.
U.S. Appl. No. 15/071,113 , "Final Office Action", dated Jul. 26, 2019, 13 pages.
U.S. Appl. No. 15/071,113 , "Final Office Action", dated Nov. 2, 2018, 13 pages.
U.S. Appl. No. 15/071,113 , "Non-Final Office Action", dated Apr. 1, 2019, 13 pages.
U.S. Appl. No. 15/071,113 , "Non-Final Office Action", dated Apr. 6, 2018, 15 pages.
U.S. Appl. No. 15/071,113 , "Non-Final Office Action", dated Jan. 10, 2020, 16 pages.
Charthad et al., "A mm-Sized Implantable Medical Device (IMD) with Ultrasonic Power Transfer and a Hybrid Bi-Directional Data Link", IEEE Journal of Solid-State Circuits, vol. 50, No. 8, Aug. 2015, 13 pages.
European Application No. 17712625.7 , "Office Action", dated Oct. 8, 2019, 6 pages.
Ho et al., "Wireless Power Transfer to Deep-Tissue Microimplants", PNAS Early Edition, vol. 111, No. 22, Jun. 3, 2014, pp. 1-6.
Mark , "Powering mm-Size Wireless Implants for Brain-Machine Interfaces", Electrical Engineering and Computer Sciences University of California at Berkley, Technical Report No. UCB/EECS2011-130, Available online at: https://www2.eecs.berkeley.edu/Pubs/TechRpts/2011/EECS-2011-130.pdf, Dec. 12, 2011, 152 pages.
Moon et al., "Novel Energy Harvesting Antenna Design Using a Parasitic Radiator", Progress in Electromagnetics Research, vol. 142, 2013, pp. 545-557.
International Application No. PCT/US2017/021403 , "International Preliminary Report on Patentability", dated Sep. 27, 2018, 8 pages.
International Application No. PCT/US2017/021403 , "International Search Report and Written Opinion", dated May 23, 2017, 14 pages.
Chinese Application No. CN201680083783.1, Notice of Decision to Grant, dated Jul. 6, 2020, 5 pages.
Chinese Application No. CN201680083783.1, Office Action, dated Sep. 29, 2019, 11 pages.

(56) References Cited

OTHER PUBLICATIONS

Chinese Application No. CN201680083783.1, Office Action, dated Apr. 10, 2019, 12 pages.
Chinese Application No. CN201680083783.1, Office Action, dated Apr. 1, 2020, 8 pages.
European Application No. EP16829381.9, Office Action, dated Jun. 4, 2019, 5 pages.
European Application No. EP16829381.9, Office Action, dated Nov. 13, 2019, 6 pages.
Japanese Application No. JP2018-559669, Notice of Decision to Grant, dated Jul. 9, 2020, 3 pages.
International Application No. PCT/US2016/069426, International Preliminary Report on Patentability, dated Aug. 16, 2018, 9 pages.
International Application No. PCT/US2016/069426, International Search Report and Written Opinion, dated Apr. 20, 2017, 11 pages.
U.S. Appl. No. 15/071,113, Final Office Action, dated Sep. 3, 2020, 16 pages.
European Application No. 16829381.9, Office Action, dated Oct. 13, 2020, 4 pages.
U.S. Appl. No. 15/071,113, Notice of Allowance, dated Mar. 1, 2021, 8 pages.
Japanese Application No. 2018-541624, Office Action, dated Mar. 12, 2021, 4 pages.
U.S. Appl. No. 15/071,113, Ex-Parte Quayle Action, dated Dec. 18, 2020, 7 pages.
European Application No. 17712625.7, Notice of Decision to Grant, dated Nov. 26, 2020, 2 pages.
European Application No. 17771637.0, "Summons to Attend Oral Proceedings", dated Mar. 31, 2021, 13 pages.
Manteghi, "Electrically Coupled Loop Antenna as A Dual for the Planar Inverted-F Antenna", Microwave and Optical Technology Letters, vol. 55, No. 6, Jun. 2013, pp. 1409-1412.
Application No. CN201780012176.0, Office Action, dated Dec. 9, 2021, 9 pages.

* cited by examiner

SYSTEMS AND METHODS FOR PROVIDING WIRELESS POWER TO DEEP IMPLANTED DEVICES

CROSS-REFERENCE TO RELATED APPLICATIONS

This application claims priority to U.S. Provisional Patent Application No. 62/393,081, filed Sep. 11, 2016, titled "Systems and Methods for Providing Wireless Power to Deep Implanted Devices," the entirety of which is hereby incorporated by reference.

BACKGROUND

The present disclosure generally relates to wireless power generation systems and methods. More specifically, and without limitation, the present disclosure relates to non-invasive systems and methods for providing wireless power to an implanted device in an individual or other living being.

Implanted devices, such as devices implanted in the body of an individual or other living being, may be used for various functions. For example, an endoscopic capsule may be implanted to perform telemetry within the gastrointestinal tract of a patient. As another example, a brain-computer interface may be implanted to augment and/or repair various cognitive and sensory-motor functions. Yet another example is a micro sensor for sensing physiological parameters of an individual. These and other implanted devices may include various subsystems for collecting data, providing outputs based on collected data, performing calculations, and/or carrying out various instructions.

Various techniques and systems exist for powering an implanted device. One technique includes providing power to an implanted device through wireless power transfer using an ex-vivo antenna. This approach has a number of challenges and shortcomings. One challenge is that the implanted device may reside deep within the body (e.g., greater than 10 mm below the surface of the skin), and therefore wireless power signals must travel through multiple layers of body tissue (including layers of skin, fat, and muscle) before reaching the implanted device. As a result, wireless power signals become increasingly attenuated as they travel through successive layers of body tissue, resulting in poor power transfer efficiency. Another challenge is that the implanted device is not externally visible, and therefore precise alignment between the ex-vivo antenna and the implanted device may be difficult to achieve. This challenge is exacerbated by body movements (e.g., caused by respiration), which may cause the implanted device to move around within the body and/or cause the ex-vivo antenna to be moved from its the initial placement.

One solution to the transfer efficiency challenge is to simply increase transmit power of the ex-vivo antenna. While this may be a viable solution in certain scenarios, it may not be desirable in the context of the human body. Indeed, various government and health regulations may limit the amount of power that can be radiated into the human body. Accordingly, existing systems and methods for providing wireless power do not address the challenge of efficiently delivering power to implanted devices, while minimizing the amount of power radiated into the human body.

SUMMARY

The present disclosure includes systems and methods for wirelessly providing power to implanted devices. In illustrative embodiments, a power system is capable of maximizing the amount of power received at an implanted device, while minimizing the rate at which radiofrequency (RF) energy is absorbed by the body in which the device is implanted.

In accordance with one example embodiment, a power system for providing wireless power to a device implanted in a body of an individual may include a first antenna loop that produces a first electromagnetic wave and at least one second antenna loop that produces a second electromagnetic wave. The first and second electromagnetic waves may interfere with one another to produce an interference pattern including interference maxima. Further, a location of at least one of the interference maxima may be at or substantially close to the device implanted in the body of the individual.

In accordance with another example embodiment, a method for providing wireless power to a device implanted in a body of an individual may include producing, by a first antenna loop, a first electromagnetic wave and producing, by at least one second antenna loop, a second electromagnetic wave. The method may further include interfering the first and second electromagnetic waves to produce an interference pattern including interference maxima. Further, a location of at least one of the interference maxima may be at or substantially close to the device implanted in the body of the individual.

In accordance with yet another example embodiment, a system for providing power to a device may include a first antenna loop and a power source configured to provide power to the first antenna loop and cause the first antenna loop to produce a first electromagnetic wave. The system may further include a plurality of second antenna loops configured to absorb a portion of the first electromagnetic wave and produce second electromagnetic waves. The first and second electromagnetic waves may interfere with one another to produce interference maxima. The system may also include an antenna controller coupled to the first antenna loop. The antenna controller may be configured to control a property of the first antenna loop so as to maintain the location of at least one of the interference maxima at or substantially close to the device implanted in the body of the individual.

Before explaining example embodiments of the present disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the conception and features upon which this disclosure is based may readily be utilized as a basis for designing other structures, methods, and systems for carrying out the several purposes of the present disclosure. Furthermore, the claims should be regarded as including such equivalent constructions insofar as they do not depart from the spirit and scope of the present disclosure.

BRIEF DESCRIPTION OF DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute part of this specification, and together with the description, illustrate and serve to explain the principles of various exemplary embodiments.

DETAILED DESCRIPTION OF EXAMPLE EMBODIMENTS

Figure 1:
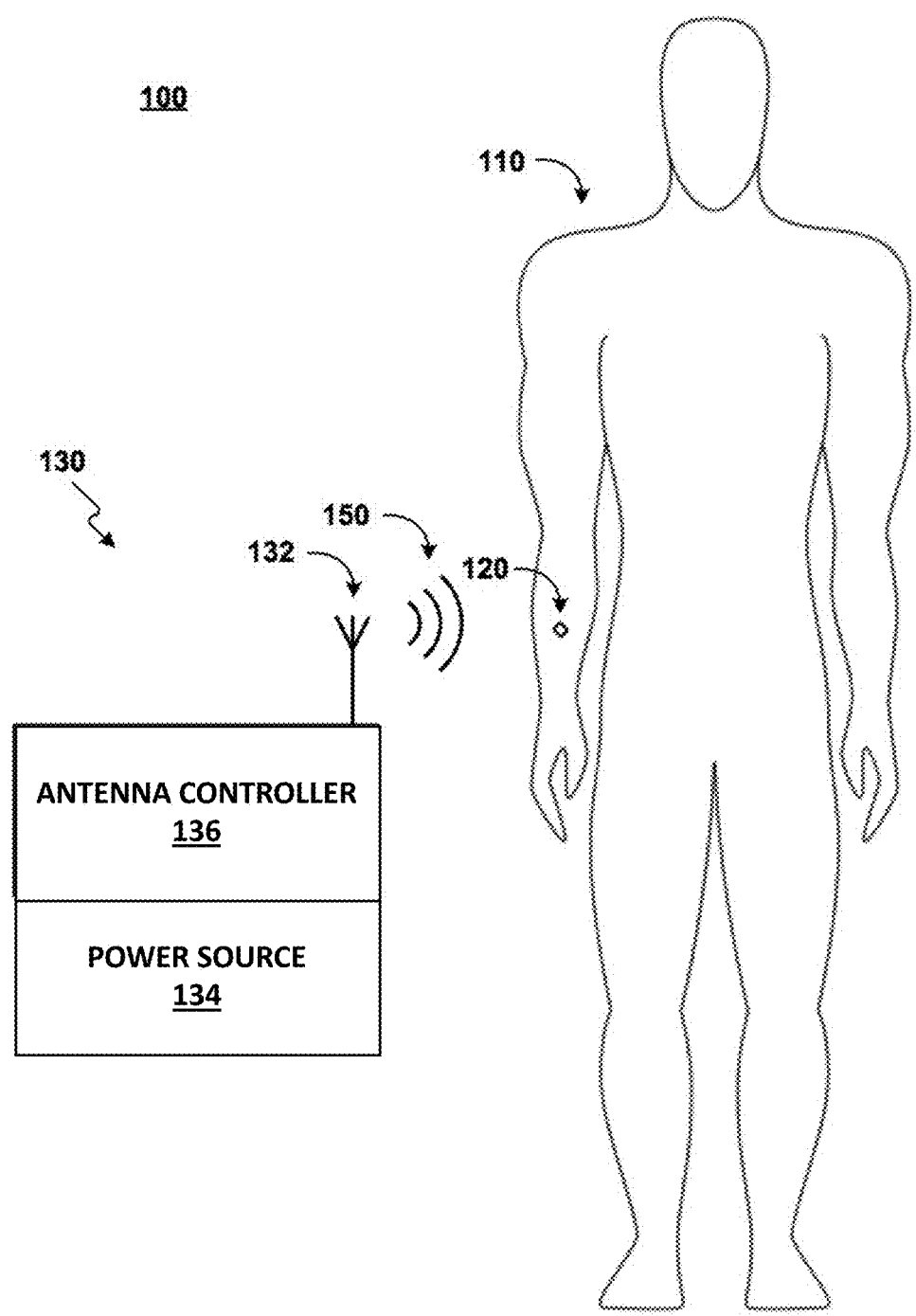
FIG. 1 is a diagram of an example system environment for implementing embodiments consistent the present disclosure.

Embodiments of the present disclosure provide improved systems and methods for providing power to implanted devices. The disclosed systems and methods are capable of maximizing the amount of power received at an implanted device, while minimizing the rate at which radiofrequency (RF) energy is absorbed by the body in which the device is implanted. Embodiments of the present disclosure are also capable of continuously providing the maximum power to devices implanted at various locations below the surface of the skin, even when the relative position of the implanted device with respect to the system providing the power changes during operation.

In accordance with some embodiments, the disclosed systems may include an ex-vivo antenna system capable of radiating power wirelessly to an implanted device. As radiated power travels further into the body, it becomes more and more attenuated. In order to combat this attenuation, and to maximize the amount of power received at the implanted device, while minimizing the amount of power absorbed by the body, the disclosed antenna system is capable of generating an interference pattern whereby at least one of the interference maxima (i.e., regions of the highest power levels) is located at or substantially close to the implanted device. In some embodiments, the interference pattern may also be generated such that the energy is broadly distributed at the surface of the skin so as to minimize the peak specific absorption rate (SAR).

The interference pattern may be generated through a combination of, for example, a primary antenna loop and one or more secondary antenna loops. The primary antenna loop may receive power generated by a power source and may radiate the power as electromagnetic waves. The secondary antenna loops (also referred to as passive radiators) absorb some of the power radiated by the primary antenna loop and reradiate the absorbed power also as electromagnetic waves. Alternatively, the secondary antenna loops may receive power generated by a power source and may radiate the power as electromagnetic waves. The electromagnetic waves produced by the primary antenna loop and the electromagnetic waves produced by the secondary antenna loop(s) interfere constructively and destructively with each other to generate the interference pattern.

Various aspects of the ex-vivo antenna system, including the primary antenna loop and the secondary antenna loops, may be designed and/or controlled during operation, such that at least one of the interference maxima is maintained at or substantially close to the implanted device, even when the relative position between the implanted device and the ex-vivo antenna system changes during operation. Additionally, or alternatively, various aspects of the ex-vivo antenna system, including the primary antenna loop and the secondary antenna loops, may be designed and/or controlled during operation, such that the energy is broadly distributed at the surface of the skin so as to minimize the peak specific absorption rate (SAR). Accordingly, the ex-vivo antenna system is capable of forming an interference pattern that broadly distributes power at the surface of the skin, while providing and maintaining focused power at or substantially close to the implanted device.

Reference will now be made in detail to embodiments according to the present disclosure, the examples of which are described herein and illustrated in the accompanying drawings. Wherever possible, the same reference numbers will be used throughout the drawings to refer to the same or like parts.

FIG. 1 depicts an example system environment 100 for implementing embodiments of the present disclosure. As shown in FIG. 1, system environment 100 includes a number of components. It will be appreciated from this disclosure that the number and arrangement of these components is exemplary only and provided for purposes of illustration. Other arrangements and numbers of components may be utilized without departing from the teachings and embodiments of the present disclosure.

As shown in the example embodiment of FIG. 1, system environment 100 includes an implanted device 120 and a power system 130. In some embodiments, implanted device 120 is positioned in a subject 110. Subject 110 may be a human subject, an animal subject, or any other type of living subject. In some embodiments, implanted device 120 may be a centimeter implanted device (i.e., a device having size dimensions at least one centimeter each), a millimeter implanted device (i.e., a device having size dimensions less than one centimeter but at least one millimeter each), or a sub-millimeter implanted device (i.e., a device having size dimensions less than one millimeter each). As illustrated in FIG. 1, implanted device 120 includes an antenna system and a rectifier for receiving power wirelessly from power system 130 and converting the received power to DC for use by subsystems of implanted device 120. Implanted device 120 may be capable of being implanted at various locations and at various depths within the body of subject 110. While implanted device 120 is shown in FIG. 1 to be implanted in the arm of subject 110, other implant locations are contemplated and the illustrated example is in no way intended to be limiting on the present disclosure. Implanted device 120 may move within the body of subject 110 after implantation.

Implanted device 120 may include one or more subsystems for performing various functions. Examples of an implanted device include a vestibular prosthesis having subsystems for augmenting and/or repairing one or more functions of a subject 110's vestibular system, a micro sensor or telemetry device having subsystems for collecting data about various bodily systems of subject 110, a brain-computer interface device having subsystems for sensing brain activity of subject 110 and converting the sensed signals to instructions for performing various physical actions, a drug delivery device, a neural stimulation device, and a pain stimulation device. Other example implanted devices may be used in conjunction with the disclosed embodiments, however, and the enumerated examples are in no way intended to be limiting on the scope of the present disclosure.

Power system 130 may include one or more ex-vivo antenna systems 132 and one or more power sources 134. Power system 130 may further include one or more antenna controllers 136. Antenna system 132 may be capable of transmitting and receiving signals at various radio frequencies using power from power source 134. For example, power source 134 may generate power and provide it to antenna system 132, and antenna system 132 may wirelessly radiate the generated power. Each power source 134 may be implemented by using any conventional power generation system, such as a portable (e.g., battery operated) or fixed (e.g., a lab power supply) power source, a variable or constant power source, etc. In some embodiments, each antenna system 132 is paired with a single power source 134. In other embodiments, a power source 134 may provide power to one or more antenna systems 132, or each antenna system 132 may receive power from one or more power sources 134.

Each antenna system 132 may include one or more antenna elements (referred to herein as loops). The design aspects of antenna system 132 (e.g., loop location, spacing, size and power, signal frequency, etc.) may be optimized for different implanted devices 120, different applications (e.g., different subjects 110), different implant locations, etc. For example, some antenna systems 132 may be designed to be held close to the skin of subject 110 (e.g., on the skin of subject 110 or a few millimeters away from the skin). Other antenna systems 132 may be designed to be held further away. Accordingly, these differences in location may drive antenna size, loop spacing, signal frequency, etc., subject to constraints of maximizing link gain and minimizing energy loss in tissue and peak specific absorption rate.

In some embodiments, one or more antenna controllers 136 may be configured to adjust, during operation, one or more properties (e.g., loading capacitances/inductances) of antenna system 132. Additionally, or alternatively, one or more antenna controllers 136 may be designed or configured to adjust, during operation, one or more properties (e.g., frequency, phase, and magnitude) of signal(s) that are fed into antenna system 132. For example, antenna system 132 may include a tunable phase shifter that changes the phase of the signals fed into antenna system 132.

The adjustments made by antenna controllers 136 may change, during operation, the location at which the power is provided by antenna system 132. Therefore, in some embodiments, antenna controller 136 may adjust antenna system 132 and/or signal(s) that are fed into antenna system 132 to compensate for any misalignment that may have been introduced between antenna system 132 and implanted device 120 during operation. A misalignment between antenna system 132 and implanted device 120 may be introduced during operation, for example, when implanted device 120 moves around within the body of subject 110, and/or when antenna system 132 is moved after the initial placement (e.g., due to body movements caused by respiration). A misalignment between antenna system 132 and implanted device 120 may also be introduced, for example, when antenna system 132 is initially misaligned with implanted device 120 (e.g., due to implanted device 120 not being externally visible). In some embodiments, such a misalignment may be determined based on a signal strength indicator received from the implanted device 120.

Transmitted signals 150 may include instructions such as, for example, instructions for implanted device 120 to perform telemetry by capturing data about the environment in which it is implanted. Transmitted signals 150 may alternatively, or in addition, include sufficient power for supplying implanted device 120 with power to run any subsystems included in implanted device 120. Received signals from implanted device 120 may include data such as, for example, sensed or measured data, still images, video, audio, etc. In addition, as indicated below, received signals from implanted device 120 may also include a signal strength indicator and/or other signals to control the delivery of power to the implanted device 120.

In some embodiments, implanted device 120 may periodically generate and send data or signals, such as a received signal strength indicator (RSSI), to antenna controller 136 of power system 130. In such embodiments, antenna controller 136 may include a control system that makes adjustments based on the RSSI information and/or other signals received from implanted device 120. The control system may be implemented by any suitable combination of hardware, software, and/or firmware (e.g., a combination of a processor with software or logic-enabled circuitry). By way of example, a control system of antenna controller 136 may make be configured to make adjustments to antenna system 132 and or the signals fed into antenna system 132 such that the RSSI is maximized at implanted device 120.

In embodiments where power system 130 includes a plurality of antenna systems 132, each antenna system may be preconfigured or arranged to initially provide power to a predetermined regions under the skin of subject 110. The predetermined regions may overlap at least partially with each other. In such embodiments, one or more antenna controllers 136, based on RSSI and/or other signals received from implanted device 120, may adjust the plurality of antenna systems 132. The RSSI signals and adjustments by the antenna controller 136 may be used to determine the implant location and facilitate alignment between the between antenna system 132 and implanted device 120.

Antenna system 132 may transmit and receive data and power using various near-field or intermediate-field transmission techniques. Such techniques may include non-radiative transmission techniques such as near/intermediate-field coupling. Examples of near/intermediate-field coupling include inductive coupling and capacitive coupling. In some embodiments, where power system 130 and implanted device 120 communicate via inductive coupling, antenna system 132 may generate a magnetic near-field to transmit data and/or power to implanted device 120. In some embodiments, where power system 130 and implanted device 120 communicate via capacitive coupling, antenna system 132 may generate an electric near-field to transmit data and/or power to implanted device 120.

Figure 2:
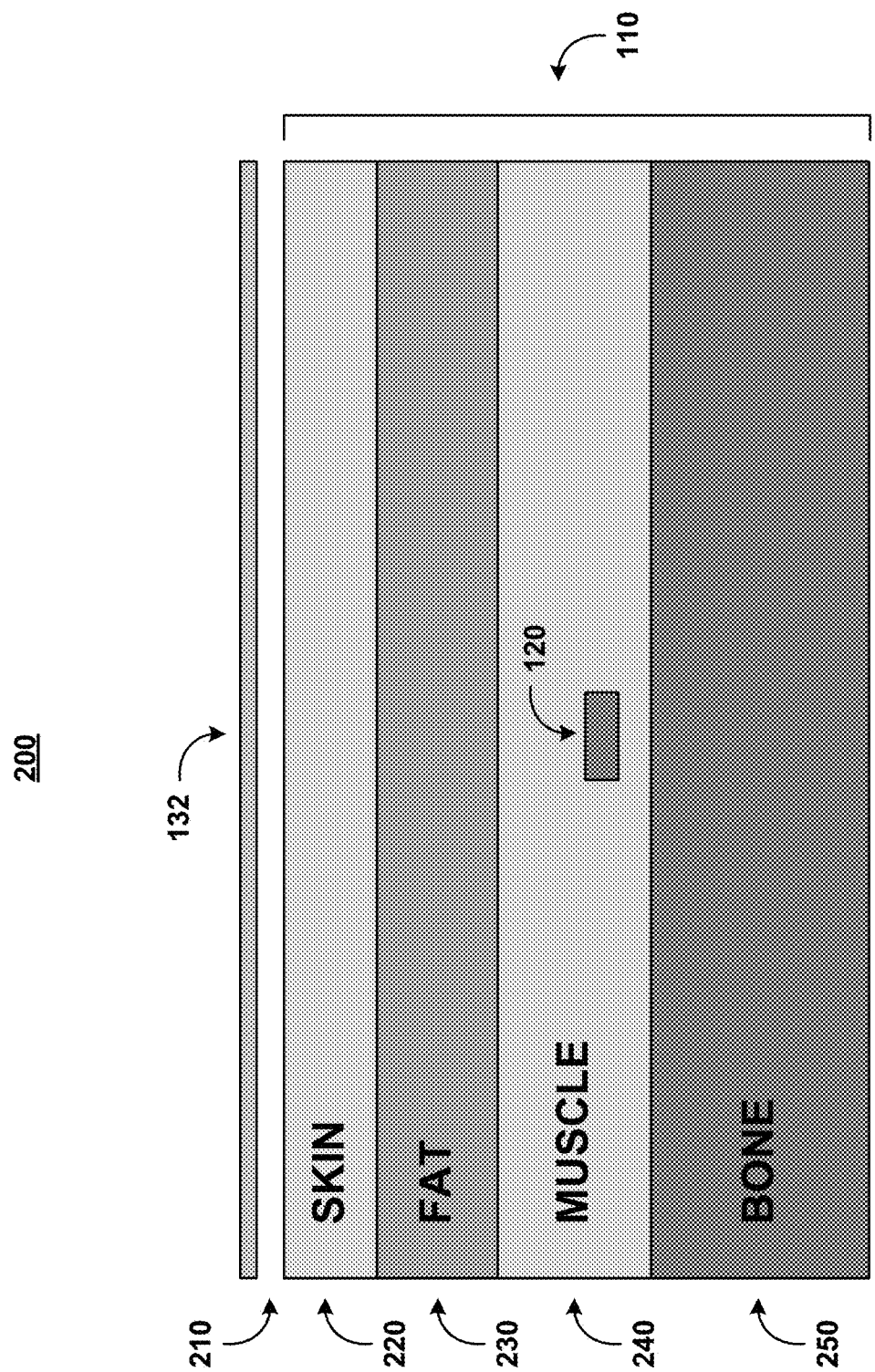
FIG. 2 is a cross-sectional view of a portion of the example system environment shown in FIG. 1.

FIG. 2 illustrates a cross-sectional view 200 of the example system environment 100 shown in FIG. 1. As shown in cross-sectional view 200, implanted device 120 may be implanted in muscle layer 240 of subject 110. Antenna system 132 may transmit power wirelessly to implanted device 120 through skin layer 220, fat layer 230, and muscle layer 240 of subject 110. Each layer 220-240 of subject 110 may provide varying levels of attenuation to the transmissions of antenna system 132. Antenna system 132 may be held close to skin layer 220 of subject 110, leaving an air gap 210 of various distances (e.g., 5-10 mm). While antenna system 132 may be held directly against skin layer 220, leaving an air gap 210 between antenna system 132 and skin layer 220 may act as an insulator that helps to minimize tuning defects and stabilizes the transmission frequency of antenna system 132. While an air gap 210 is used to isolate antenna system 132 from skin layer 220 in the example shown in FIG. 2, other electrical insulators may be used. Examples of electrical isolators include, glass, ceramic, paper, A.B.S., acrylic, fiberglass, and nylon. In some embodiments, antenna system 132 may be packed in an insulating material to achieve similar results from providing air gap 210.

Since skin layer 220, fat layer 230, and muscle layer 240 are opaque, implanted device 120 may not be externally visible after it is implanted in the body of subject 110. Therefore, accurately aligning antenna system 132 with implanted device 120 may be difficult, and a misalignment may be introduced between antenna system 132 and implanted device 120 during the initial placement of antenna system 132 over the skin of subject 110. Such a misalignment results in inefficient transfer of power from antenna system 132 to implanted device 120. A misalignment between antenna system 132 and implanted device 120 may also result during operation, for example, because of movement of implanted device 120 and/or antenna system 132 away from their initial position(s).

Therefore, consistent with embodiments of the present disclosure, antenna controller 136 may be configured to adjust antenna system 132, during operation, to improve the alignment and location at which the power is provided by antenna system 132 in relation to implanted device 120. Further details on how antenna controller 36 adjusts antenna system 132 and corrects misalignments with implanted device 120 are provided herein with reference to example embodiments.

Figure 3:
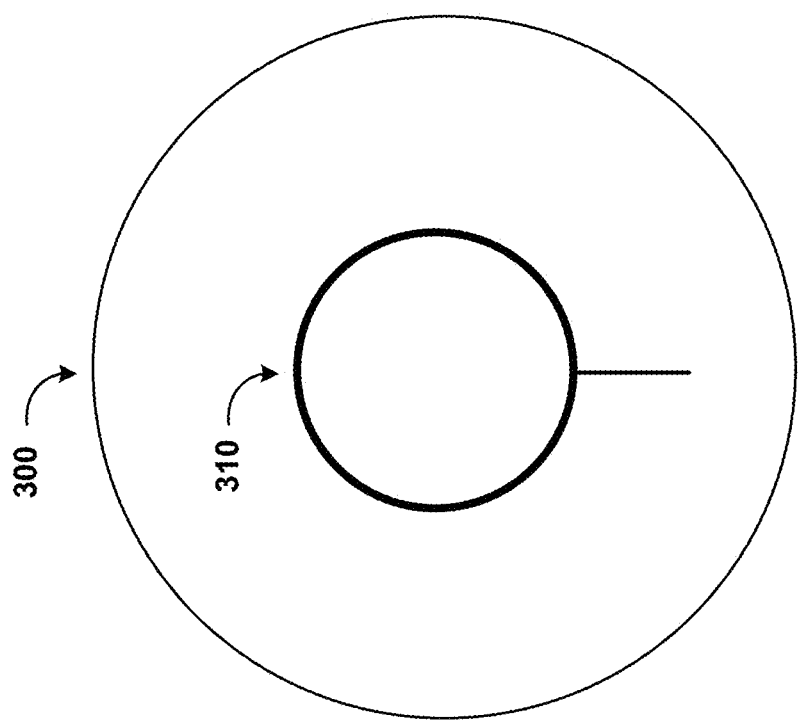
FIG. 3 is an illustration of an example antenna system for providing wireless power with a single loop design that lacks beam focusing characteristics.

FIG. 3 illustrates an example antenna system 300 with a single antenna loop 310 for providing power to an implanted device. Loop 310 may be circular in shape and may be physically coupled to the surface of one side of antenna system 300. A power source may provide power to antenna system 300. Antenna system 300 may provide the power wirelessly to one or more implanted devices by radiating the power through loop 310. In some embodiments, loop 310 may be any other closed shape or configuration, such as, but not limited to, triangles, rectangles, squares, and hexagons.

Figure 4A:
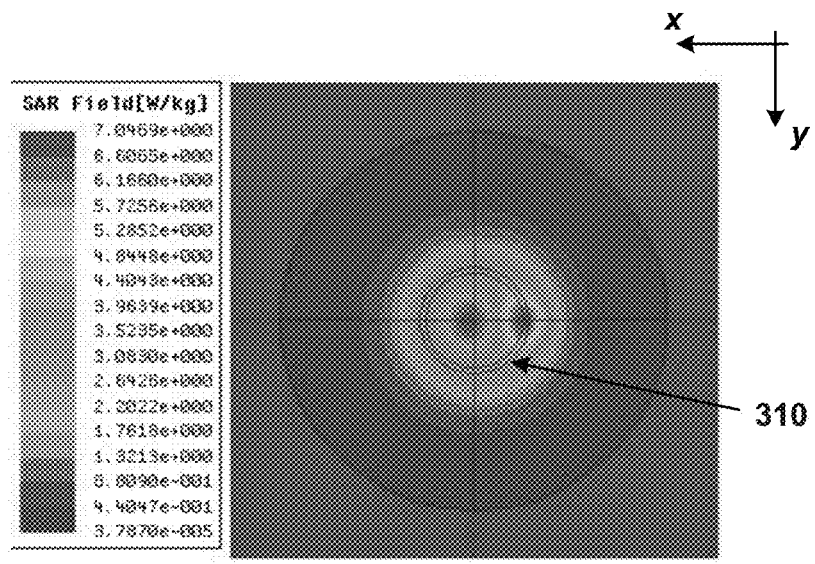
FIGS. 4A and 4B illustrate various performance characteristics of the example antenna system illustrated in FIG. 3.
Figure 4B:
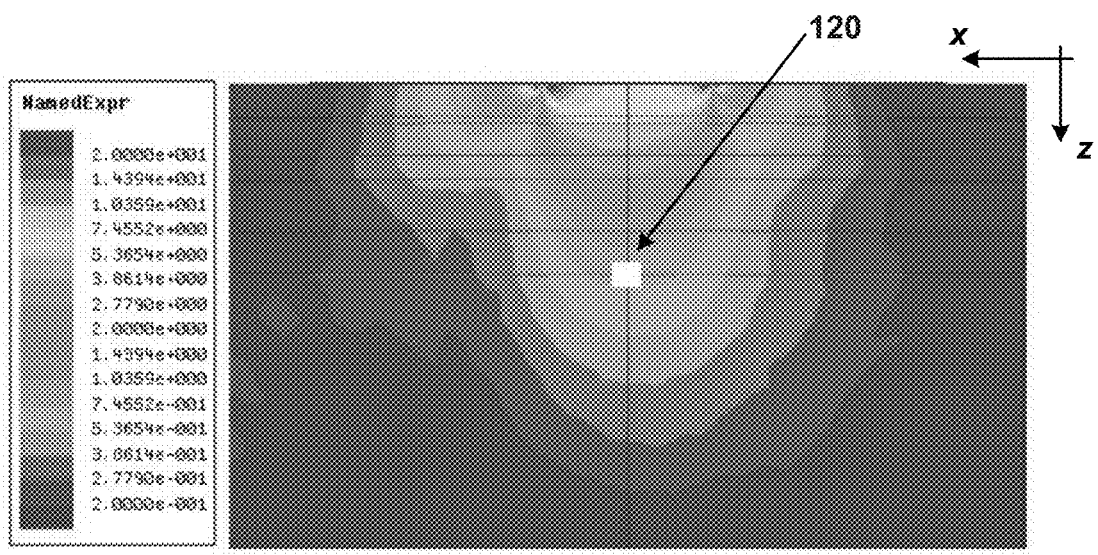

FIGS. 4A and 4B are graphical representations of various performance characteristics associated with single loop, antenna system 300 of FIG. 3. FIG. 4A is a heat map showing a top-down view of the specific absorption rate and distribution of the RF electromagnetic energy radiated by antenna system 300. The intensity of the heat map represents the specific absorption rate (SAR), which is the rate at which the RF electromagnetic energy is absorbed into the human body. As shown in FIG. 4A, the power distribution of antenna system 300 is mostly uniform around loop 310 with the exception of a hotspot at the left side of loop 310. Power intensity drops off quickly, however, as it radiates inwardly and away from loop 310, resulting in poor distribution uniformity in the x-y plane.

FIG. 4B is a heat map showing a cross-sectional view of the SAR and distribution of electromagnetic energy radiated by single loop, antenna system 300. As shown in FIG. 4B, the specific absorption rate of antenna system 300 drops of quickly as the transmitted electromagnetic energy radiates into the body toward implanted device 120. One of the primary causes of the poor signal penetration of antenna system 300 is a lack of power focusing capabilities. A significant amount of power is radiated away from the implanted device, thereby resulting in poor power transfer efficiency and increased specific absorption rate.

Figure 5B:
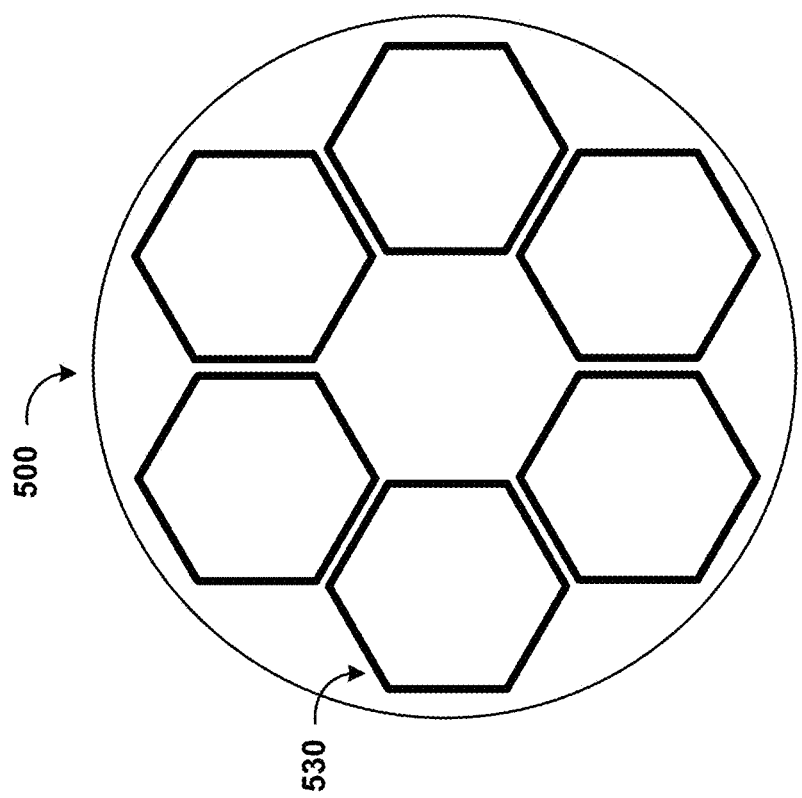
FIGS. 5A and 5B illustrate an example embodiment of an antenna system for providing wireless power, in accordance with embodiments of the present disclosure.
Figure 5A:
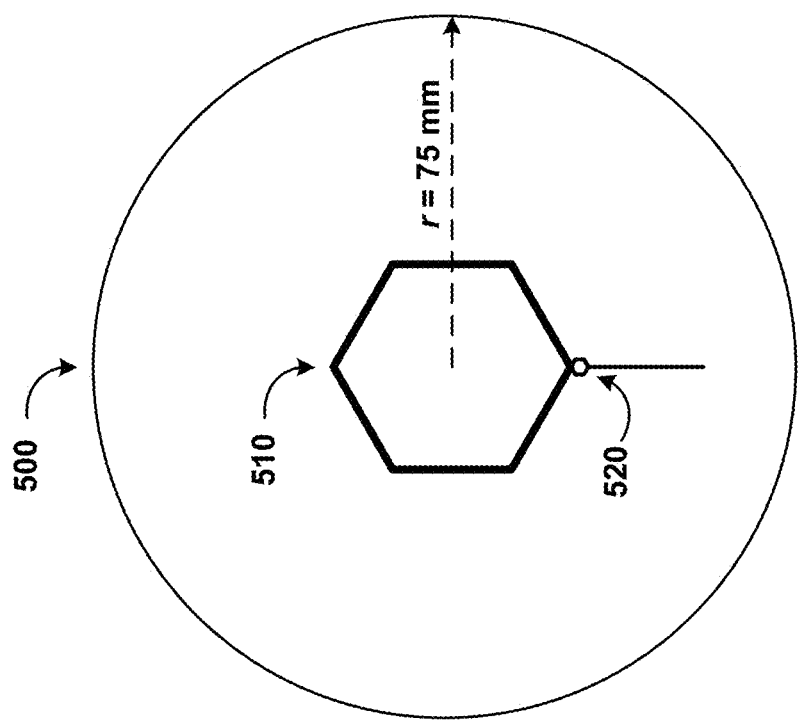

FIGS. 5A and 5B illustrate an example antenna system 500, in accordance with embodiments of the present disclosure. Antenna system 500 may be used to implement one or more aspects of antenna system 132 of FIG. 1, while addressing one or more of the shortcomings of antenna system 300 described above. As shown in FIGS. 5A and 5B, antenna system 500 includes a primary antenna loop 510 and one or more secondary antenna loops 530. It will be appreciated from this disclosure that the number and arrangement of these components is exemplary only and provided for purposes of illustration. Other arrangements and numbers of components may be utilized without departing from the teachings and embodiments of the present disclosure. By way of example, in some embodiments antenna system 500 may be implemented as a disc-shaped structure having a radius of approximately 75 mm, as shown in FIG. 5A. Other dimensions and structures may be implemented, consistent with the teachings of this disclosure.

FIG. 5A illustrates a primary side of antenna system 500. Primary antenna loop 510 includes a matching network 520, and primary antenna loop 510 and/or matching network 520 may be physically coupled to the surface of the primary side. A power source (e.g., power source 134 of FIG. 1) may provide power to primary antenna loop 510 through matching network 520, causing primary antenna loop 510 to produce electromagnetic waves. Matching network 520 may be implemented as a network of electrical circuit components (e.g., capacitors, resistors, inductors, etc.) and may be used to match the impedance of antenna system 500 to the input impedance of the power source at the desired operating frequency. Accordingly, the configuration of components included in matching network 520 may depend on various design characteristics, such as transmit frequency of antenna system 500, the size and placement of primary antenna loop 510 and secondary antenna loops 530, the tissue properties, the spacing between the loop and the tissue, including any air gaps and housing material thickness, etc.

FIG. 5B illustrates a secondary side of antenna system 500. In some embodiments, the secondary side may be a side of antenna system 500 opposing the primary side. In some embodiments, the secondary side may be a layer stacked on top of the primary side. As shown in FIG. 5B, one or more secondary antenna loops 530 may be physically coupled to the surface of the secondary side. Secondary antenna loops 530 may be positioned so as to absorb some of the power radiated by primary antenna loop 510 that would otherwise be radiated away from implanted device 120 and absorbed by the body of subject 110. Secondary antenna loops 530 may reradiate the absorbed power as electromagnetic waves.

In some embodiments, one or more secondary antenna loops 530 may each include a matching network (not shown in FIG. 5B) similar to matching network 520. Further, these secondary antenna loops may be coupled to one or more power sources, providing power to each of the secondary antenna loops 530 and causing each of them to produce electromagnetic waves.

According to embodiments of the present disclosure, the electromagnetic waves produced by secondary antenna loops 530 and primary antenna loop 510 may interfere constructively and destructively with each other to generate an interference pattern. The generated interference pattern may include regions of interference maxima, where the electromagnetic waves interfere constructively, and regions of interference minima, where the waves interfere destructively.

Various design characteristics of antenna system 500 may affect the inductive and the capacitive coupling properties between secondary antenna loops 530 and between primary antenna loop 510 and secondary antenna loops 530, which, in turn, affect the interference pattern generated by antenna system 500. For example, some design characteristics of antenna system 500 may affect the locations and/or intensities of the interference maxima and minima. Accordingly, the design characteristics of antenna system 500 may be determined to accommodate different shapes and sizes of implanted devices 120, different implant depths (and differing levels of attenuation by extension), different locations at which antenna system 500 is intended to be held (e.g., on the skin, close to the skin, etc.), variations in the patient's anatomy, including thickness of skin, fat, and muscle tissue, as well as to ensure that the power system (e.g., power system 130 of FIG. 1) for antenna systems 500 complies with all applicable government and health/safety laws and regulations. The phrase "design characteristics" refers to characteristics of antenna system 500 that are determined prior to the fabrication of antenna system 500, and therefore cannot be changed during operation.

One design characteristic that affects the coupling properties is the size of primary antenna loop 510 and secondary antenna loops 530. For example, while primary antenna loop 510 and secondary antenna loops 530 are shown in FIGS. 5A and 5B to all be the same size, primary antenna loop 510 and one or more secondary antenna loops 530 may be different sizes and/or one or more secondary antenna loops 530 may be different in size. The number of primary elements 510 and/or secondary antenna loops 530 included in antenna system 500 may also be adjusted (e.g., increased or decreased). Another design characteristic that affects the coupling properties is the spacing between primary antenna loop 510 and secondary antenna loops 530 and/or the spacing between secondary antenna loops 530. For example, while there is no overlap between primary antenna loop 510 and secondary antenna loops 530 in FIGS. 5A and 5B, one or more secondary antenna loops 530 may overlap each other, one or more secondary antenna loops 530 and primary antenna loop 510 may overlap each other, or any combination thereof. A further design characteristic that affects the coupling properties is the shapes of primary antenna loop 510 and secondary antenna loops 530. For example, primary antenna loop 510 and secondary antenna loops 530 may be hexagonal, square, circular, or any other symmetrical, asymmetrical, or amorphous shapes, or a combination thereof. The orientation of primary antenna loop 510 and/or secondary antenna loops 530 may also affect the inductive and the capacitive coupling properties. For example, while primary antenna loop 510 and secondary antenna loops 530 are shown in FIGS. 5A and 5B to be parallel with each other on the x-y plane, any of primary antenna loop 510 and secondary antenna loops 530 may be rotated about one or more three-dimensional axes.

Even when one or a combination of various design characteristics of antenna system 500 are optimized to maximize the power provided to the initial implant location of implanted device 120, a misalignment between implanted device 120 and antenna system 500 may be introduced during operation. As discussed herein, such a misalignment may cause inefficient transfer of power from antenna system 500 to implanted device 120. As further explained below with reference to FIGS. 6A, 6B and 6C, one or more properties of antenna system 500 (e.g., loading capacitances/inductances) and/or one or more properties (e.g., frequency, phase, and magnitude) of the signal(s) that are fed into antenna system 500 may be adjusted. These adjustments may be made by antenna controller 136 and may cause the locations and/or intensities of the interference maxima and minima to change. Therefore, as discussed above, these adjustments may be used to compensate for the misalignment introduced during operation.

Antenna system 500 may be implemented through various configurations and electromechanical structures. For example, antenna system 500 may include a substrate such as a ridged printed circuit board or a flexible substrate formed to the body shape of a subject 110 wearing antenna system 500. The size and shape of the substrate may be selected according to one or more design parameters (e.g., the size and depth of the implanted device to be powered, the amount of power required by the implanted device, etc.). Primary antenna loop 510, matching network 520, and secondary antenna loops 530 may be printed thereon. Elements 510-530 may be printed using one or more types of ridged and/or flexible conductive materials such as, for example, copper, gold, silver, aluminum, etc. While primary antenna loop 510 and matching network 520 may be printed on the opposite side of the substrate as secondary antenna loops 530, other configurations are contemplated without departing from the scope of this disclosure. For example, elements 510-530 may be all printed on the same side of the substrate or one or more secondary antenna loops 530 may be printed on opposing sides of the substrate.

In addition, additional layers of antenna loops may be added to antenna system 500. For example, an antenna system having a substrate with multiple stacked layers deposited thereon may have a first layer deposited on the substrate that includes a primary antenna loop 510, a second layer including one or more secondary antenna loops 530 deposited on top of the primary antenna loop 510 layer, and one or more layers of additional secondary antenna loops 530 deposited on top of the first layer of secondary antenna loops 530. Each layer of secondary antenna loops 530 may have design characteristics (e.g., size, shape, spacing, and number of secondary antenna loops 530, etc.) similar to, or different from, one or more of the other layers of secondary antenna loops 530.

Figure 6B:
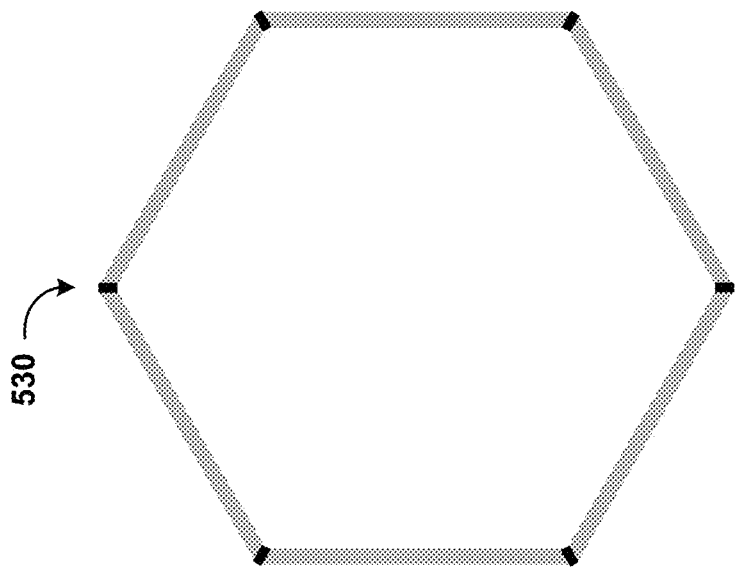
FIGS. 6A, 6B, and 6C illustrate detailed views of example antenna loops, in accordance with embodiments of the present disclosure.
Figure 6A:
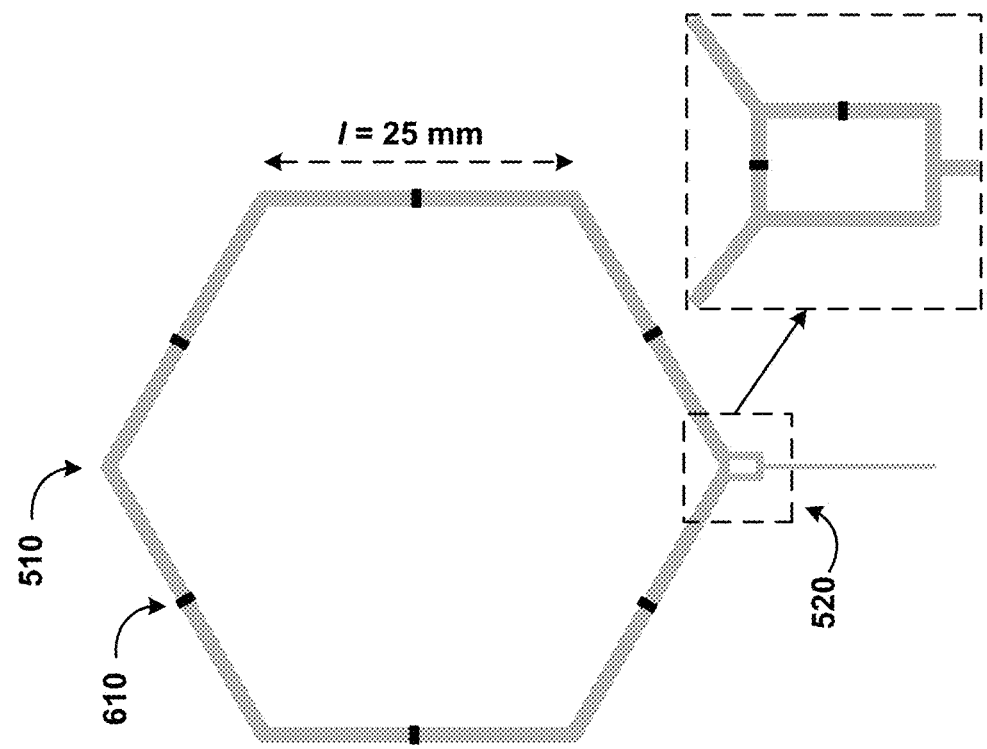
Figure 6C:
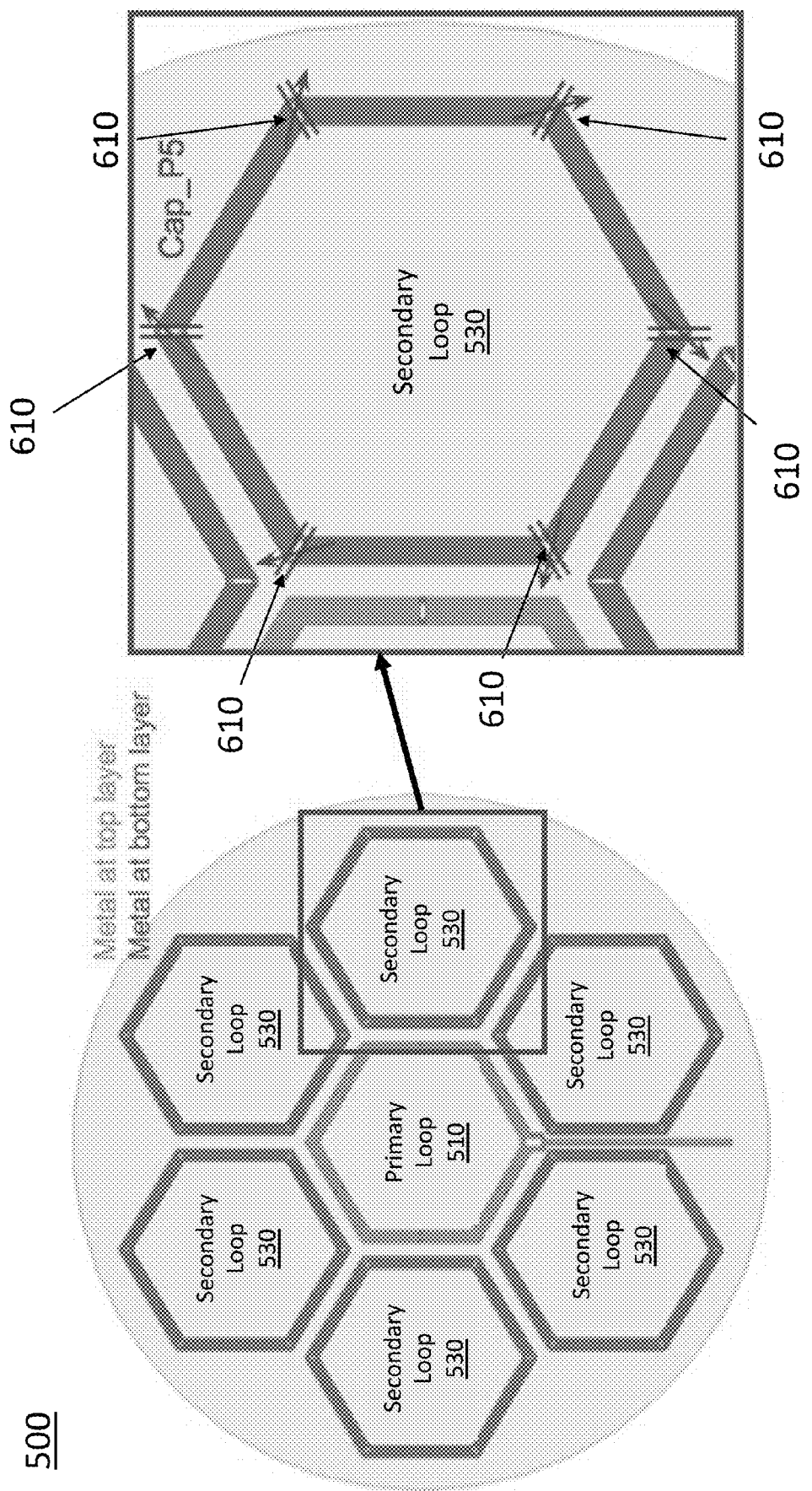

FIGS. 6A and 6B respectively illustrate detailed views of primary antenna loop 510 and a secondary antenna loop 530 of antenna array 500 shown in FIGS. 5A and 5B. FIG. 6C illustrates both primary loop 510 and secondary antenna loops 530 of antenna array 500 shown in FIGS. 6A and 6B.

As shown in the example embodiments of FIGS. 6A, 6B, and 6C, primary antenna loop 510 and secondary antenna loop 530 may be implemented as hexagonally-shaped structures. By way of example, each segment of the hexagonal structure may have a length of approximately 25 mm, as shown in FIG. 6A. As will be appreciated, other dimensions and structure shapes may be implemented, consistent with the teachings of this disclosure.

In some embodiments, primary antenna loop 510, matching network 520, and/or secondary antenna loop 530 may include one or more loading components 610. Loading components 610 may include capacitors, inductors, resistors, and/or other electronic circuit components. The characteristics (e.g., capacitance, inductance, etc.) and placement of loading components 610 may affect the loading capacitances/inductances of primary antenna loop 510 and secondary antenna loops 530. Further, the loading capacitances/inductances of primary antenna loop 510 and secondary antenna loops 530 may affect the properties of the electromagnetic waves (e.g., magnitude and phase) produced by primary antenna loop 510 and secondary antenna loops 530, which, in turn, affect the interference pattern. For example, the relative loading capacitances/inductances of primary antenna loop 510 and secondary antenna loops 530 may affect the locations and/or intensities of the interference maxima and minima of the interference pattern.

In some embodiments, characteristics of one or more loading components 610 may be adjustable by antenna controller 136 during operation. For example, one or more loading components 610 may be a voltage-controlled variable capacitor/inductor, and antenna controller 136 may be coupled to, and configured to control, the voltage-controlled variable capacitor/inductor. Additionally, or alternatively, loading component 610 may be, for example, a digitally tunable capacitor or any other variable reactive element.

Accordingly, in some embodiments, antenna controller 136 may indirectly adjust the loading capacitance/inductance of an antenna loop during operation since the characteristics of the loading components 610 determine the loading capacitance/inductance of the antenna loop. Furthermore, antenna controller 136 may also indirectly adjust the locations and/or intensities of the interference maxima and minima of the interference pattern as they are affected by the relative loading capacitances/inductances of the primary and secondary antenna loops. As discussed above, these adjustments may be used to compensate for misalignment between implanted device 120 and antenna system 500.

In some embodiments, as shown in FIG. 6C, loading components 610 of one or more secondary antenna loops 530 may be adjustable during operation, while loading components 610 of primary antenna loop 510 are fixed. For example, loading components 610 of secondary loops 530 may be variable capacitors, while loading components 610 of primary loop 510 may be elements with fixed capacitances. In some embodiments, characteristics of loading components 610 within a single antenna loop (primary or secondary) may be the same or substantially the same. For example, as shown in FIG. 6C, loading components 610 of secondary loops 530 may be variable capacitors that have the same initial capacitance and/or loading components 610 of primary loop 510 may be elements that have the same, fixed capacitance values.

In some embodiments, loading components 610 of a subset of secondary antenna loops 530 may be adjustable during operation, while loading components of the remaining secondary antenna loops 530 are fixed. In some embodiments, all loading components may be adjustable during operation. Further, in some embodiments, a single antenna controller 136 may be coupled to and configured to adjust loading components 610 of a single loop (primary or secondary). Also, in some embodiments, a single antenna controller 136 may be coupled to and configured to adjust loading components 610 of one or more antenna loops (e.g., the primary and/or secondary loops).

As discussed above, one or more secondary antenna loops 530 may each include a matching network (not shown in FIG. 5B) similar to matching network 520. Further, as discussed above, these secondary antenna loops may be coupled to one or more power sources, causing each to produce electromagnetic waves. In such embodiments, power loss from mutual coupling may be higher compared to embodiments where the secondary loops 530 are not powered by power sources.

Consistent with some embodiments of the present disclosure, antenna controller 136 may be configured to adjust one or more properties of the signal(s) provided to each of the secondary antenna loops 630. For example, antenna controller 136 may be configured to adjust the frequency, phase, and/or magnitude of the signal provided to each of the secondary antenna loops 630. Also, in some embodiments, antenna controller 136 may be a tunable phase shifter.

As will be appreciated from the present disclosure, the frequency, phase, and/or magnitude of the signal fed into primary antenna loop 510 and secondary antenna loops 530 affect the properties of the electromagnetic waves (e.g., the magnitude and phase of such waves) produced by primary antenna loop 510 and secondary antenna loops 530, which, in turn, affect the interference pattern. Therefore, adjustments to the frequency, phase, and/or magnitude of the signals fed into the antenna loops may also indirectly change the locations and/or intensities of the interference maxima and minima of the interference pattern. Accordingly, consistent with some embodiments, antenna controller 136 may indirectly adjust the locations and/or intensities of the interference maxima and minima of the interference pattern as they are affected by the frequency, phase, and/or magnitude of the signals fed into the antenna loops.

Figure 7A:
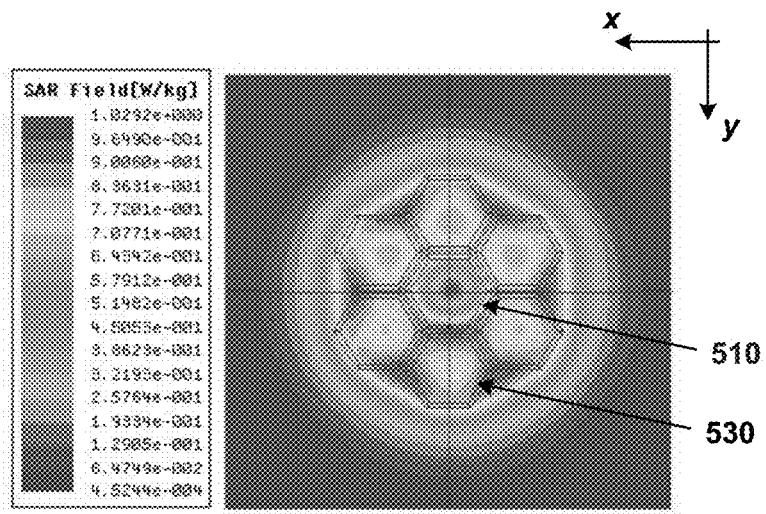
FIGS. 7A and 7B illustrate various performance characteristics associated with the example antenna system shown in FIGS. 5A and 5B.
Figure 7B:
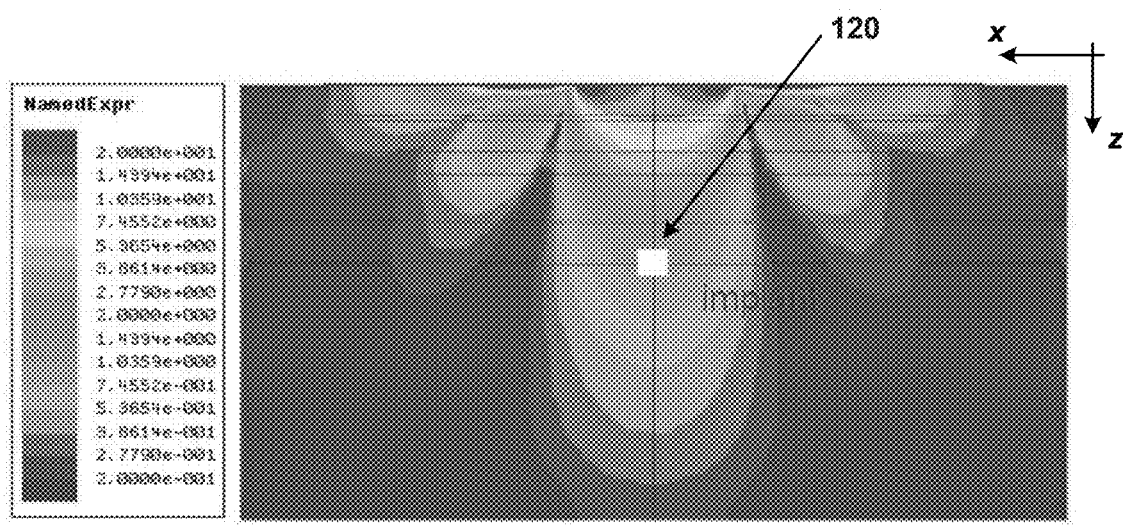

FIGS. 7A and 7B are graphical representations of various performance characteristics associated with antenna system 500 of FIGS. 5A and 5B. In FIGS. 7A-7B, implanted device 120 is directly below primary antenna loop 510. FIG. 7A is a heat map showing a top-down view of the specific absorption rate and distribution of the RF electromagnetic energy radiated by antenna system 500. FIG. 7B is a heat map showing a cross-sectional view of the specific absorption rate and distribution of the RF electromagnetic energy radiated by antenna system 500. In FIGS. 7A and 7B, primary antenna loop 510 has a loading capacitance of 8 pF and all of secondary antenna loops 530 have a loading capacitance of 7.5 pF.

As shown in FIGS. 7A and 7B, the power radiated by antenna system 500 is distributed broadly and uniformly around primary antenna loop 510 and secondary antenna loops 530 at the surface of the skin of subject 110. Therefore, for a given power transmission level, the power absorbed by human tissue per area or per volume (as a measurement of SAR) is significantly less for antenna system 500's power transmission compared to antenna system 300. In some embodiments, the maximum SAR caused by at least one of the first electromagnetic wave or the second electromagnetic wave is below or equal to 1.6 watts per kilogram. Moreover, the power provided by antenna system 500, unlike antenna system 300, is focused at the location of implanted device 120 due to the constructive interference pattern generated by secondary antenna loops 530. Accordingly, a greater power transfer efficiency to implanted device 120 compared to the power transfer efficiency of antenna system 300 is achieved while minimizing power loss into the body of subject 110.

Figure 8A:
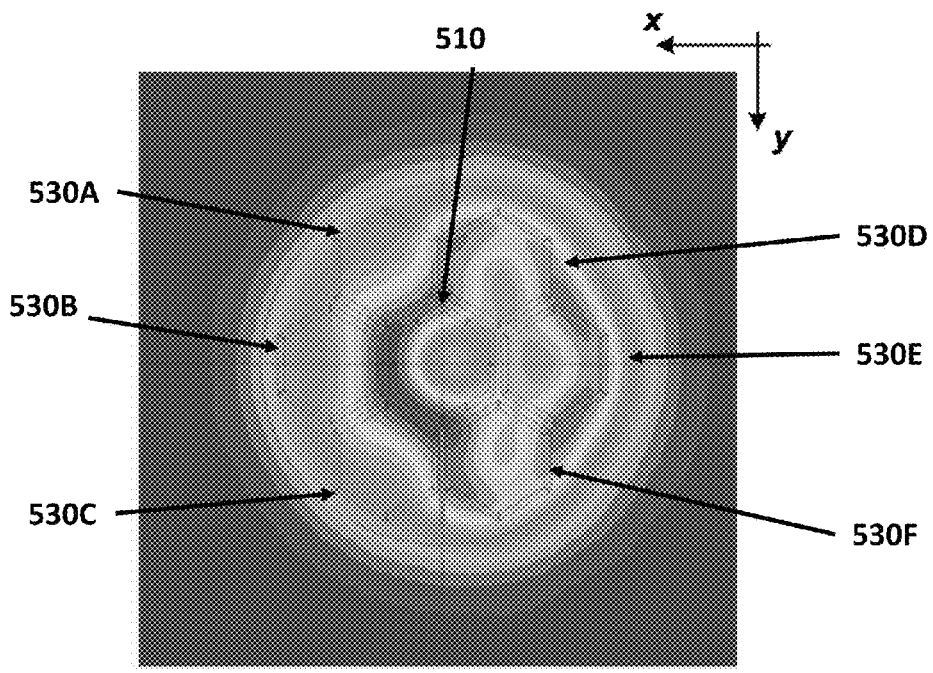
FIGS. 8A and 8B illustrate further characteristics associated with the example antenna system shown in FIGS. 5A and 5B as a result of the implanted device being moved and the loading capacitances of the secondary antenna loops being changed.
Figure 8B:
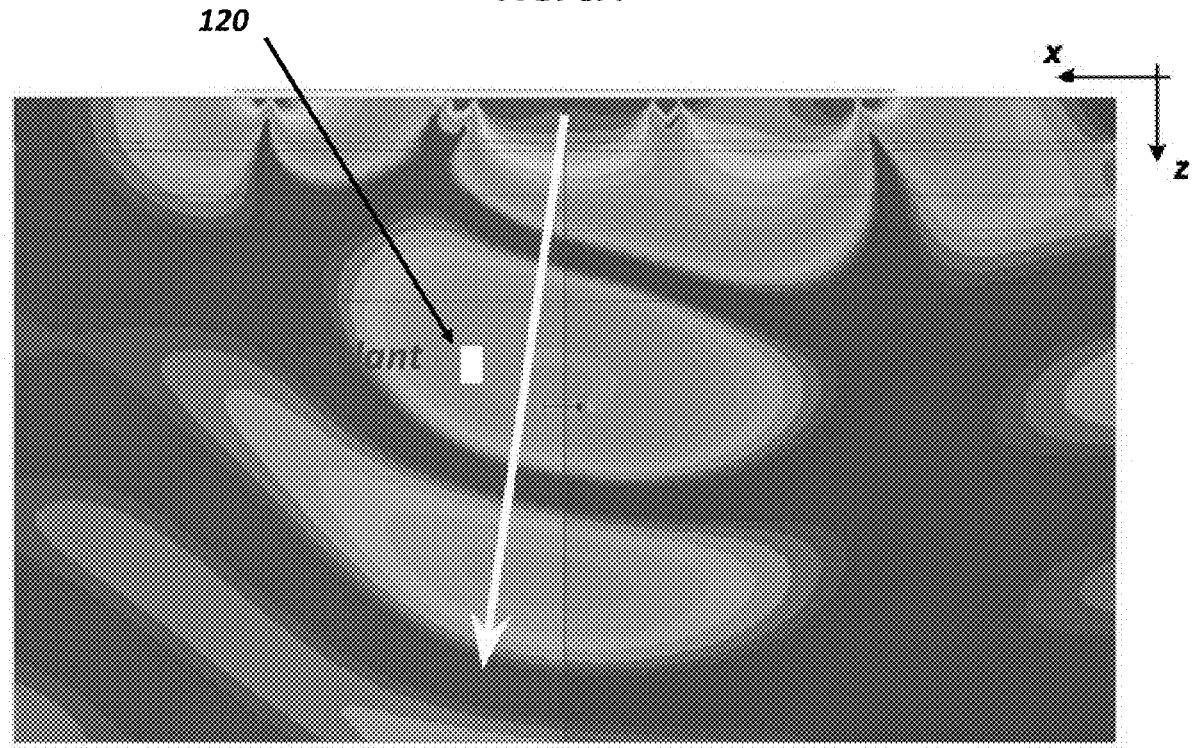

FIGS. 8A and 8B illustrate further characteristics associated with the example antenna system shown in FIGS. 5A and 5B as a result of implanted device 120 being moved and the loading capacitances of secondary antenna loops 530 being changed. Specifically, in FIGS. 8A and 8B, the loading capacitances of secondary antenna loops 530 have been adjusted (e.g., during operation) such that the location of one of the interference maxima is over the new position of implanted device 120. In the illustrations of FIGS. 8A and 8B, the loading capacitance of primary antenna loop 610 remains unchanged (i.e., 8 pF) from that illustrated in FIGS. 7A and 7B. However, secondary antenna loops 530A-C now have a loading capacitance of 9.0 pF, and secondary antenna loops 530D-F have a loading capacitance of 7.0 pF. In some embodiments, adjustments to the loading capacitances of secondary antenna loops 530A-F may be made by one or more antenna controllers 136. As further shown in FIGS. 8A and 8B, the power radiated by antenna system 500 remains broadly and uniformly distributed around primary antenna loop 510 and secondary antenna loops 530 at the surface of the skin of subject 110.

Figure 9:
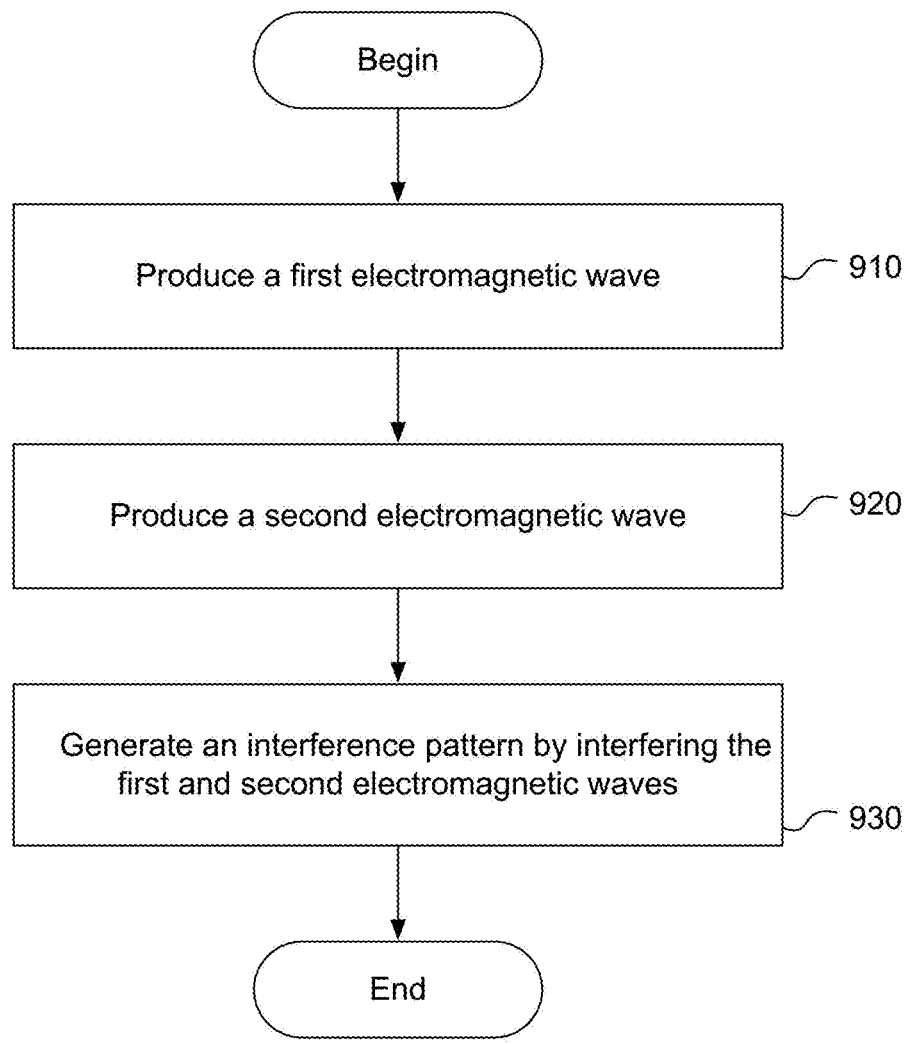
FIG. 9 is a flow diagram of an example process for providing wireless power to a device implanted in a body of an individual, in accordance with an embodiment of the present disclosure.

FIG. 9 is a flow diagram of an example process 900 for providing wireless power to a device implanted in a body of an individual, in accordance with an embodiment of the present disclosure. Example process 900 may be implemented using antenna system 500 and the other various features and aspects disclosed herein. As illustrated in FIG. 9, at step 910, a first electromagnetic wave is produced. For example, a first antenna loop, such as primary antenna loop 510, may be controlled to produce a first electromagnetic wave. At step 920, a second electromagnetic wave is produced. For example, at least one of the secondary antenna loops 530 may be controlled to produce a second electromagnetic wave. Then, at step 930, an interference pattern is generated by interfering the first and second electromagnetic wave. The interference pattern may include interference maxima located at or substantially close to an implanted device (such as implanted device 120) in the body of the individual. As disclosed herein, antenna controller 136 may be configure to control one or more properties of the antenna loop(s) to adjust the interference pattern caused the first and second electromagnetic waves to interfering with one another. Also, in some embodiments, alignment may be performed, during operation, so that the interference maxima of the interference pattern is at or substantially close to the implanted device in the body of the individual.

As part of step 930, antenna controller 136 may control a property of the first antenna loop (e.g., primary antenna loop 510) so as to maintain the location of the one of the interference maxima at or substantially close to implanted device 120. In some embodiments, the controlled property of the first antenna loop may include a reactance of a reactive element associated with the first antenna loop. For example, the reactive element may be one of a variable capacitor or a variable inductor. Also, in some embodiments, the controlled property of the first antenna loop may include a loading capacitance or a loading inductance.

As part of step 930 or another step in process 900, antenna controller 136 may control a property of a signal for the first antenna loop so as to maintain the location of the one of the interference maxima at or substantially close to the implanted device 120. In some embodiments, the property of the signal includes at least one of a frequency, phase, or magnitude of the signal. Also, in some embodiments, a maximum power at a skin of the body of the individual caused by at least one of the first electromagnetic wave or the second electromagnetic wave may be less than a power at the one of interference maxima. Further, in some embodiments, a maximum SAR caused by at least one of the first electromagnetic wave or the second electromagnetic wave may be below or equal to 1.6 watts per kilogram.

In the preceding specification, various exemplary embodiments and features have been described with reference to the accompanying drawings. It will, however, be evident that various modifications and changes may be made thereto, and additional embodiments and features may be implemented, without departing from the broader scope of the invention as set forth in the claims that follow. For example, advantageous results still could be if components in the disclosed systems were combined in a different manner and/or replaced or supplemented by other components. Other implementations are also within the scope of the following exemplary claims. The specification and drawings are accordingly to be regarded in an illustrative rather than restrictive sense. Moreover, it is intended that the disclosed embodiments and examples be considered as exemplary only, with a true scope of the present disclosure being indicated by the following claims and their equivalents.

What is claimed is:

1. A power system for providing wireless power to a device implanted in a body of an individual, comprising:
   a power source;
   one or more antenna controllers;
   a first antenna loop electrically coupled to a first antenna controller of the one or more antenna controllers, the first antennal loop comprising a first loading component, the first antenna controller configured to control a characteristic of the first loading component of the first antenna loop to produce a first electromagnetic near-field; and
   at least one second antenna loop electrically coupled to a second antenna controller of the one or more antenna controllers, the second antenna controller configured to control the second antenna loop to produce a second electromagnetic near-field,
   the first and second antenna controllers configured to control the first and second antenna loops simultaneously to generate the first and second electromagnetic near-fields that will interfere with one another to produce an interference pattern including interference maxima, at least one of the interference maxima having a location at a depth associated with the device implanted in the body of the individual, wherein the interference pattern is broadly distributed at the surface of the skin to minimize a peak specific absorption rate at the surface of the skin.

2. The power system of claim 1, wherein the first antenna controller is configured to control a reactance of a reactive element associated with the first antenna loop.

3. The power system of claim 2, wherein the reactive element is one of a variable capacitor or a variable inductor.

4. The power system of claim 1, wherein the first antenna controller is configured to control a loading capacitance or a loading inductance.

5. The power system of claim 1, wherein the first antenna controller is further configured to control a property of a signal for the first antenna loop in order to maintain a location of at least one of the interference maxima substantially at the depth.

6. The power system of claim 5, wherein the property of the signal for the first antenna loop includes at least one of a frequency, phase, or magnitude of the signal for the first antenna loop.

7. The power system of claim 5, wherein the first antenna controller includes a tunable phase shifter.

8. The power system of claim 1, wherein the first and second antenna controllers are configured to generate first and second electromagnetic near-fields, respectively, having a maximum power at a depth associated with skin of the body of the individual to be less than a power associated with at least one of the interference maxima.

9. The power system of claim 1, wherein a maximum specific absorption rate (SAR) caused by at least one of the first electromagnetic near-field or the second electromagnetic near-field is below or equal to 1.6 watts per kilogram.

10. A method for providing wireless power to a device implanted in a body of an individual, comprising:
    controlling, using a first antenna controller of one or more antenna controllers, a loading component of a first antenna loop applying power by a first antenna controller to produce a first electromagnetic near-field, the first antenna loop electrically coupled to the first antenna controller;
    simultaneously with controlling the loading component of the first antenna loop, controlling a second antenna loop by a second antenna controller of the one or more antenna controllers to produce a second electromagnetic near-field, the first and second electromagnetic near-fields interfering with one another to produce an interference pattern including interference maxima, the second antenna loop electrically coupled to the second antenna controller;
    wherein a location of at least one of the interference maxima is at a depth associated with the device implanted in the body of the individual; and
    wherein the interference pattern is broadly distributed at the surface of the skin to minimize a peak specific absorption rate at the surface of the skin.

11. The method of claim 10, wherein controlling the loading component comprises controlling a reactance of a reactive element associated with the first antenna loop.

12. The method of claim 11, wherein the reactive element is one of a variable capacitor or a variable inductor.

13. The method of claim 10, wherein controlling the loading component of the first antenna loop includes controlling a loading capacitance or a loading inductance.

14. The method of claim 10, further comprising:
    controlling, using the first antenna controller, a property of a signal for the first antenna loop so as to maintain the location of at least one of the interference maxima at the device implanted in the body of the individual.

15. The method of claim 14, wherein the property of the signal for the first antenna loop includes at least one of a frequency, phase, or magnitude of the signal for the first antenna loop.

16. The method of claim 10, wherein the first and second antenna controllers are configured to generate first and second electromagnetic near-fields, respectively, having a maximum power at a depth associated with skin of the body of the individual to be less than a power associated with at least one of the interference maxima.

17. The method of claim 10, wherein a maximum specific absorption rate (SAR) caused by at least one of the first electromagnetic near-field or the second electromagnetic near-field is below or equal to 1.6 watts per kilogram.

18. A system for providing power to a device implanted in a body of an individual, comprising:
    a first antenna loop, the first antennal loop comprising a first loading component;
    a plurality of second antenna loops;
    a power source configured to provide power to the first antenna loop and to the plurality of second antenna loops, the first antenna loop configured to produce a first electromagnetic near-field and the plurality of second antenna loops configured to produce a plurality of second electromagnetic near-fields; and
    a first antenna controller coupled to the first antenna loop, the first antenna controller being configured to control a characteristic of the first loading component to produce the first electromagnetic near-field;
    a plurality of second antenna controllers, each second antenna controller of the plurality of second antenna controllers coupled to different one of the plurality of second antennas, each second antenna controller of the plurality of the second antenna controllers being configured to control a property of a respective second antenna loop; and
    wherein the first electromagnetic near-field and the plurality of second electromagnetic near-fields configured to cause a specific absorption rate ("SAR") at a first depth corresponding to a skin surface below a threshold maximum SAR and to interfere with one another to produce interference maxima and the first antenna controller and the plurality of second antenna controllers configured to maintain a location of at least one of the interference maxima at or close to a second depth associated with the device implanted in the body of the individual.

* * * * *